(12) United States Patent
Krohn et al.

(10) Patent No.: US 12,048,756 B2
(45) Date of Patent: Jul. 30, 2024

(54) PIGMENT SUSPENSION AND METHOD FOR DYING KERATINOUS MATERIAL USING THE PIGMENT SUSPENSION

(71) Applicant: Henkel AG & Co. KGaA, Duesseldorf (DE)

(72) Inventors: Rene Krohn, Norderstedt (DE); Thomas Hippe, Appen (DE); Jessica Brender, Hamburg (DE); Stefan Hoepfner, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 114 days.

(21) Appl. No.: 17/785,875

(22) PCT Filed: Oct. 16, 2020

(86) PCT No.: PCT/EP2020/079172
§ 371 (c)(1),
(2) Date: Jun. 15, 2022

(87) PCT Pub. No.: WO2021/121720
PCT Pub. Date: Jun. 24, 2021

(65) Prior Publication Data
US 2023/0065273 A1  Mar. 2, 2023

(30) Foreign Application Priority Data
Dec. 16, 2019  (DE) ............... 10 2019 219 712.4

(51) Int. Cl.
| | | |
|---|---|---|
| *A61Q 5/10* | (2006.01) | |
| *A61K 8/25* | (2006.01) | |
| *A61K 8/34* | (2006.01) | |
| *A61K 8/58* | (2006.01) | |
| *A61K 8/73* | (2006.01) | |
| *A61K 8/81* | (2006.01) | |

(52) U.S. Cl.
CPC ............... *A61K 8/25* (2013.01); *A61K 8/345* (2013.01); *A61K 8/585* (2013.01); *A61K 8/731* (2013.01); *A61K 8/8147* (2013.01); *A61Q 5/10* (2013.01); *A61K 2800/43* (2013.01); *A61K 2800/884* (2013.01); *A61K 2800/95* (2013.01)

(58) Field of Classification Search
CPC .......... A61K 8/25; A61K 8/345; A61K 8/585; A61K 8/731; A61K 8/8147; A61K 2800/43; A61K 2800/884; A61K 2800/95; A61K 8/044; A61K 8/19; A61K 8/34; A61Q 5/10; A61Q 5/06
See application file for complete search history.

(56) References Cited

U.S. PATENT DOCUMENTS

2010/0083446 A1* 4/2010 Brun ............... A61K 8/891
8/405

FOREIGN PATENT DOCUMENTS

| | | |
|---|---|---|
| DE | 102018207025 A1 | 11/2019 |
| WO | 2016133812 A1 | 8/2016 |

* cited by examiner

*Primary Examiner* — Eisa B Elhilo
(74) *Attorney, Agent, or Firm* — Lorenz & Kopf, LLP

(57) ABSTRACT

A pigment suspension is provided. In one example, the pigment suspension includes a) at least one colorant compound selected from the group of pigments, b) at least one $C_1$-$C_{10}$ alcohol, c) at least one diol, d) at least one thickening agent, and e) water. A method for dyeing keratinous material and a multi-component packaging unit (kit-of-parts) for dyeing keratinous material including a pigment suspension are also provided.

11 Claims, No Drawings

PIGMENT SUSPENSION AND METHOD FOR DYING KERATINOUS MATERIAL USING THE PIGMENT SUSPENSION

CROSS-REFERENCE TO RELATED APPLICATION

This application is a U.S. National-Stage entry under 35 U.S.C. § 371 based on International Application No. PCT/EP2020/079172, filed Oct. 16, 2020, which was published under PCT Article 21(2) and which claims priority to German Application No. 10 2019219712.4, filed Dec. 16, 2019, which are all hereby incorporated in their entirety by reference.

TECHNICAL FIELD

The subject of the present application is a pigment suspension comprising a pigment and a carrier medium. Another subject matter is a method for dyeing keratinous material using the pigment suspension.

BACKGROUND

Pigments, especially metal-containing pigments, are frequently used in coatings, paints, printing inks, powder coatings, cosmetics or plastics for coloration. Paints, varnishes, printing inks, cosmetics and powder coatings are liquid or powder coating materials that are applied to surfaces to obtain both improved or altered optical and physical properties.

Changing the shape and color of keratinous fibers, especially hair, is an important area of modern cosmetics. To change the color of the hair, the specialist knows various coloring systems, depending on the requirements of coloring. For permanent, intensive dyeings with good fastness properties and good gray coverage, oxidation dyes are usually used. Such colorants usually contain oxidation dye precursors, so-called developer components and coupler components, which form the actual dyes under the influence of oxidizing agents such as hydrogen peroxide among themselves. Oxidation dyes are exemplified by very long-lasting dyeing results.

When using direct dyes, already formed dyes diffuse from the colorant into the hair fiber. Compared to oxidative hair dyeing, the dyeings obtained with direct dyes have lower durability and faster washout. Colorations with direct dyes usually remain on the hair for a period of between 5 and 20 washes.

For short-term color changes on the hair and/or skin, the use of color pigments is known. Color pigments are insoluble, color-imparting substances. These are present undissolved in the form of small particles in the coloring formulation and are merely deposited externally on the hair fibers and/or skin surface. Therefore, they can usually be removed without residue by a few washes with surfactant-containing cleaning agents. Various products of this type are available on the market under the name of hair mascara.

Metallic luster pigments or metallic effect pigments are widely used in many fields of technology. They are used, for example, to color coatings, printing inks, inks, plastics, glasses, ceramic products and preparations for decorative cosmetics such as nail polish. They are exemplified above all by their attractive angle-dependent color impression (goniochromism) and their metallic-looking luster.

Hair with a metallic finish or metallic highlights are in trend. The metallic tone makes the hair look thicker and shinier.

For applications in the cosmetic field, for example in the color modification of keratin fibers with pigments, it is important that the pigments are provided to the user in a storage-stable and dosage-capable form. This can be done in particular in the form of a storage-stable pigment suspension.

Ground pigment powders and water are usually used for the production of inorganic pigment suspensions. If necessary, organic or inorganic dispersing aids must be added in small quantities.

BRIEF SUMMARY

In an exemplary embodiment, a pigment suspension is provided. The pigment suspension includes a) at least one colorant compound selected from the group of pigments, b) at least one C1-C10 alcohol, c) at least one diol, d) at least one thickening agent, and e) water.

In another exemplary embodiment, a method for dyeing keratinous material, in particular human hair, is provided. The method includes applying an agent (a) to the keratinous material. The agent (a) includes (a1) at least one organic C1-C6-alkoxysilane. An agent (b) is applied to the keratinous material. The agent (b) includes (b1) at least one sealing reagent. At least one of the agent (a) and the agent (b) further includes a pigment suspension including a) at least one colorant compound selected from the group of pigments, b) at least one $C_1$-$C_{10}$ alcohol, c) at least one diol, d) at least one thickening agent, and e) water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It is the task of the present disclosure to provide pigment suspensions that can be prepared easily and inexpensively and are stable in storage. In particular, the pigments should not agglomerate and/or settle. The carrier medium and any auxiliaries should be compatible with the application modalities of the pigment suspension.

Pigment suspensions comprising a $C_1$-$C_{10}$ alcohol, a diol and water as carrier medium and a thickener have been shown to meet these requirements.

Accordingly, a first object of this application comprises
  a) at least one colorant compound selected from the group of pigments,
  b) at least one $C_1$-$C_{10}$ alcohol,
  c) at least one diol,
  d) at least one thickening agent and
  e) water.

The first primary ingredient as per the present disclosure are the pigment suspensions, which contain at least one colorant compound from the group of pigments.

Pigments within the meaning of the present disclosure are colorant compounds which have a solubility in water at 25° C. of less than 0.5 g/L, preferably less than 0.1 g/L, still more preferably less than 0.05 g/L. Water solubility, for example, can be done using the method described below: 0.5 g of the pigment is weighed out in a beaker. A stirring bar is added. Then one liter of distilled water is added. This mixture is heated to 25° C. for one hour with stirring on a magnetic stirrer. If undissolved components of the pigment are still visible in the mixture after this period, the solubility of the pigment is below 0.5 g/L. If the pigment-water mixture cannot be visually assessed due to the high intensity of the pigment, which may be finely dispersed, the mixture is filtered. If a portion of undissolved pigment remains on the filter paper, the solubility of the pigment is below 0.5 g/L.

Suitable pigments can be of inorganic and/or organic origin.

The at least one pigment preferably has a substrate platelet.

In principle, the substrate platelet can be made of any material that can be formed into a platelet shape.

They can be of natural origin, but also synthetically produced. Materials from which the substrate platelets can be constructed include metals and metal alloys, metal oxides, preferably aluminum oxide, inorganic compounds and minerals such as mica and (semi-)precious stones, and plastics. Preferably, the substrate platelets are constructed of a metal or alloy or a mica or glass. The mica can be of natural or synthetic origin.

Accordingly, it may be preferred that the pigment comprises a substrate platelet, wherein the substrate platelet comprises a metal, metal alloy, natural mica or synthetic mica. In particular, the substrate plate is preferably made of a metal, a metal alloy, a natural mica, a synthetic mica, or glass.

Any metal suitable for pigments can be used. Such metals include iron and steel, as well as all air- and water-resistant (semi)metals such as platinum, tin, zinc, chromium, molybdenum and silicon, as well as their alloys such as aluminum bronzes and brass. Preferred metals are aluminum, copper, silver and gold.

In a particularly preferred embodiment, the pigment comprises a substrate platelet of a metal, wherein the metal is selected from the group of aluminum, copper, silver and gold, with substrate platelets of aluminum being particularly preferred.

Substrate platelets made of aluminum can be produced, among other things, by punching out of aluminum foil or according to common milling and atomization techniques. For example, aluminum flakes are available from the Hall process, a wet milling process.

In another preferred embodiment, the pigment has a metal alloy substrate plate, wherein the metal alloy comprises brass.

In a particularly preferred embodiment, the pigment comprises a substrate platelet of a mica, wherein a substrate platelet of synthetic mica (INCI: Synthetic Fluorophlogopite) is particularly preferred.

A substrate wafer made of metal or a metal alloy preferably has an average thickness of at most about 150 nm, preferably less than about 50 nm, more preferably less than about 30 nm, further preferably at most about 25 nm, for example at most about 20 nm. The average thickness of the substrate platelets is at least about 1 nm, preferably at least about 2.5 nm, further preferably at least about 5 nm, for example at least about 10 nm. Preferred ranges for substrate wafer thickness are about 2.5 to about 50 nm, about 5 to about 50 nm, about 10 to about 50 nm; about 2.5 to about 30 nm, about 5 to about 30 nm, about 10 to about 30 nm; about 2.5 to about 25 nm, about 5 to about 25 nm, about 10 to about 25 nm, about 2.5 to about 20 nm, about 5 to about 20 nm, and about 10 to about 20 nm. Preferably, each substrate plate has a thickness that is as uniform as possible.

A substrate platelet of mica preferably has an average thickness of about 50 to about 1500 nm and more preferably about 90 to about 1000 nm.

The size of the substrate platelet can be tailored to the specific application, for example the desired effect on a keratinous material. Typically, the substrate platelets made of metal or a metal alloy have an average largest diameter of about about 2 to about 200 µm, especially about about 5 to about 100 µm. Typically, the substrate platelets of a mica have an average largest diameter of about about 1 to about 200 µm, particularly about about 5 to about 100 µm, and even more preferably about about 5 to about 25 µm.

In a preferred embodiment, the shape factor (aspect ratio), expressed by the ratio of the average size to the average thickness, is at least about 80, preferably at least about 200, more preferably at least about 500, further preferably more than about 750. Here, the average size of the uncoated substrate platelets is the d50 value of the uncoated substrate platelets. Unless otherwise stated, the d50 value was determined using a Sympatec Helos instrument with Quixel wet dispersion. For sample preparation, the sample to be analyzed was predispersed in isopropanol for a period of 3 minutes.

The substrate platelets can have different shapes. For example, lamellar or lenticular metal platelets or so-called vacuum metallized pigments (VMP) can be used as substrate platelets. Lamellar substrate platelets are exemplified by an irregularly structured edge and are also referred to as "comflakes" due to their appearance. Lenticular substrate platelets have an essentially regular round edge and are also referred to as "silverdollars" due to their appearance.

The metal or metal alloy substrate platelets can be passivated, for example by anodizing (oxide layer) or chromating.

A coating can change the surface properties and/or optical properties of the pigment and increase the mechanical and chemical resistance of the pigments. For example, only the top and/or bottom of the substrate wafer may be coated, with the side surfaces recessed. Preferably, the entire surface of the optionally passivated substrate platelets, including the side surfaces, is covered by the layer. The substrate platelets are preferably completely encased by the coating.

The coating may include one or more layers. In a preferred embodiment, the coating has only layer A. In a likewise preferred embodiment, the coating has a total of at least two, preferably two or three, layers. It may be preferred to have the coating have two layers A and B, with layer B being different from layer A. Preferably, layer A is located between layer B and the surface of the substrate wafer. In yet another preferred embodiment, the coating has three layers A, B, and C. In this embodiment, layer A is located between layer B and the surface of the substrate wafer, and layer C is located on top of layer B, which is different from the layer B below.

Suitable materials for layers A and, if necessary, B and C are all substances that can be permanently applied to the substrate platelets. The materials should preferably be film-applicable. Preferably, the entire surface of the optionally passivated substrate wafer, including the side surfaces, is enveloped by layer A or by layers A and B or by layers A, B and C.

In particular, the layers may each contain at least one metal oxide (hydrate).

It is preferred that the metal oxide (hydrate) is selected from the group of silicon (di)oxide, silicon oxide hydrate, aluminum oxide, aluminum oxide hydrate, boron oxide, germanium oxide, manganese oxide, magnesium oxide, iron oxide, cobalt oxide, chromium oxide, titanium dioxide, vanadium oxide, zirconium oxide, tin oxide, zinc oxide and mixtures thereof.

In the case of pigments with a substrate platelet made of metal or a metal alloy, layer A preferably has at least one low-refractive metal oxide and/or metal oxide hydrate. Low refractive index materials have a refractive index of 1.8 or less, preferably 1.6 or less.

Low refractive index metal oxide (hydrate) suitable for Layer A include, for example, silicon (di)oxide, silicon oxide hydrate, aluminum oxide, aluminum oxide hydrate, boron oxide, germanium oxide, manganese oxide, magnesium oxide, and mixtures thereof, with silicon dioxide being preferred. Layer A preferably has a thickness of about 1 to about 100 nm, further preferably about 5 to about 50 nm, especially preferably about 5 to about 20 nm.

Layer B, if present, is different from layer A and, in the case of pigments with a substrate platelet of metal or metal alloy, may contain at least one highly refractive metal oxide (hydrate). Highly refractive materials have a refractive index of at least about 1.9, preferably at least about 2.0, and more preferably at least about 2.4. Preferably, layer B comprises at least about 95 wt %, more preferably at least about 99 wt %, of high refractive index metal oxide(s).

If the layer B comprises a (highly refractive) metal oxide, it preferably has a thickness of at least has a thickness of at least about 50 nm. Preferably, the thickness of layer B is no more than about 400 nm, more preferably no more than about 300 nm.

Highly refractive metal oxides suitable for layer B are, for example, selectively light-absorbing (i.e. colored) metal oxides, such as iron(III) oxide (α- and γ-Fe2O3, red), cobalt(II) oxide (blue), chromium(III) oxide (green), titanium(III) oxide (blue, usually present in admixture with titanium oxynitrides and titanium nitrides), and vanadium (V) oxide (orange), as well as mixtures thereof. Colorless high-index oxides such as titanium dioxide and/or zirconium oxide are also suitable.

Layer B can contain a selectively absorbing dye in addition to a highly refractive metal oxide, preferably 0.001 to 5% by weight, further preferably 0.01 to 1% by weight, in each case based on the total amount of layer B. Suitable dyes are organic and inorganic dyes that can be stably incorporated into a metal oxide coating. Dyes according to the present disclosure have a solubility in water (760 mmHg) at 25° C. of more than 0.5 g/L and are therefore not to be regarded as pigments.

As an alternative to a metal oxide, layer B in the case of pigments with a substrate platelet made of metal or a metal alloy may comprise a metal particle carrier layer with metal particles deposited on the surface of the metal particle carrier layer. In a preferred embodiment, the metal particles directly cover a portion of the metal particle support layer. In this embodiment, the effect pigment has areas where there are no metal particles, i.e. areas that are not covered with the metal particles.

The metal particle support layer comprise a metal layer and/or a metal oxide layer.

When the metal particle support layer comprises a metal layer and a metal oxide layer, the arrangement of these layers is not limited.

It is preferred that the metal particle support layer comprises at least one metal layer. It is further preferred that the metal layer comprises an element selected from tin (Sn), palladium (Pd), platinum (Pt) and gold (Au).

The metal layer can be formed, for example, by adding alkali to a metal salt solution comprising the metal.

If the metal particle support layer comprises a metal oxide layer, it preferably does not comprise silica. The metal oxide layer preferably comprises an oxide of at least one element selected from the group of Mg (magnesium), Sn (tin), Zn (zinc), Co (cobalt), Ni (nickel), Fe (iron), Zr (zirconium), Ti (titanium), and Ce (cerium). Particularly preferably, the metal particle support layer iii) in the form of a metal oxide layer comprises a metal oxide of Sn, Zn, Ti and Ce.

The metal particle support layer in the form of a metal oxide layer can be prepared, for example, by hydrolyzing an alkoxide of a metal that forms the metal of the metal oxide in a sol-gel process.

The thickness of the metal layer is preferably not more than about 30 nm.

The metal particles may comprise at least one element selected from the group of aluminum (Al), titanium (Ti), chromium (Cr), iron (Fe), cobalt (Co), nickel (Ni), copper (Cu), zinc (Zn), ruthenium (Ru), rhodium (Rh), palladium (Pd), silver (Ag), tin (Sn), platinum (Pt), gold (Au), and alloys thereof. It is particularly preferred that the metal particles comprise at least one element selected from copper (Cu), nickel (Ni) and silver (Ag).

The average particle diameter of the metal particles is preferably not more than 50 nm, more preferably not more than 30 nm. The distance between the metal particles is preferably not more than 10 nm.

Suitable methods for forming the metal particles include vacuum evaporation, sputtering, chemical vapor deposition (CVD), electroless plating, or the like. Of these methods, electroless plating is particularly preferred.

According to a preferred embodiment, the pigments with a substrate platelet of metal or a metal alloy have a further layer C comprising a metal oxide (hydrate), which is different from the underlying layer B. Suitable metal oxides include silicon (di)oxide, silicon oxide hydrate, aluminum oxide, aluminum oxide hydrate, zinc oxide, tin oxide, titanium dioxide, zirconium oxide, iron (III) oxide, and chromium (III) oxide. Silicon dioxide is preferred.

In the case of pigments with a substrate platelet made of metal or a metal alloy, layer C preferably has a thickness of 10 to 500 nm, further preferably 50 to 300 nm.

In the case of pigments with a substrate platelet of mica, in particular synthetic mica, layer A comprises a metal oxide (hydrate) selected from the group of titanium dioxide ($TiO_2$), iron oxide ($Fe_2O_3$ and/or $Fe_3O_4$) and mixtures thereof. In a very preferred embodiment, layer A comprises titanium dioxide ($TiO_2$) and/or iron oxide ($Fe_2O_3$). In a highly preferred embodiment, layer A comprises titanium dioxide ($TiO_2$).

Layer B, if present, is also different from the first metal oxide (hydrate) layer in the case of pigments with a substrate platelet of mica.

Metal oxide (hydrate)s suitable for layer B are tin oxide ($SnO_2$), silicon oxide ($SiO_2$), aluminum oxide ($Al_2O_3$) and/or iron oxide ($Fe_2O_3$ and/or $Fe_3O_4$). Accordingly, it is preferred that layer B comprises a metal oxide (hydrate) selected from the group of tin oxide ($SnO_2$), silicon oxide ($SiO_2$), aluminum oxide ($Al_2O_3$), iron oxide ($Fe_2O_3$ and/or $Fe_3O_4$), and mixtures thereof. It is particularly preferred that layer B comprises tin oxide ($SnO_2$) in the case of pigments with a substrate platelet of mica, preferably synthetic mica.

Layer B may further comprise a selectively absorbing dye or pigment. Suitable dyes and/or pigments include, for example, carmine, ferric hexacyanidoferrate(II/III), and chromium oxide green ($Cr_2O_3$).

The pigments with a substrate platelet of mica may have another layer C, which acts as a protective layer and comprises a metal oxide (hydrate) or a polymer, for example a synthetic resin. Suitable metal oxide (hydrates)s include silicon (di)oxide, silicon oxide hydrate, aluminum oxide, aluminum oxide hydrate, zinc oxide, tin oxide, titanium dioxide, zirconium oxide, iron (III) oxide, and chromium (III) oxide. Silicon dioxide is preferred.

It is particularly preferred that a pigment with a substrate platelet of synthetic mica (INCI: Synthetic Fluorophlogopite) has a layer A comprising titanium dioxide ($TiO_2$).

It is also preferred that a pigment with a substrate platelet of synthetic mica (INCI: Synthetic Fluorophlogopite) has a layer A comprising iron(III) oxide ($Fe_2O_3$).

It is also preferred that a pigment with a substrate platelet of synthetic mica (INCI: Synthetic Fluorophlogopite) has a layer A comprising titanium dioxide ($TiO_2$) and iron(III) oxide ($Fe_2O_3$), and a layer B comprising tin dioxide ($SnO_2$).

It is highly preferred that a pigment with a substrate platelet of synthetic mica (INCI: Synthetic Fluorophlogopite) has a layer A comprising titanium dioxide ($TiO_2$) and a layer B comprising tin dioxide ($SnO_2$).

Preferably suitable pigments with a substrate platelet of synthetic mica are, for example, Timiron® SynWhite Satincolorona® SynCopper and/or Colorona® SynBronze from Merck.

The amount of pigment in the pigment suspension depends in particular on the type of pigment(s) and its intended use. Preferably, the amount of pigment is between about 1 and about 90% by weight, more preferably between 5 and 80% by weight and most preferably between about 10 and about 70% by weight, in each case based on the total weight of the pigment suspension.

In addition to the above-mentioned, particularly preferred pigments with substrate platelets of metal, a metal alloy or mica, other color-imparting compounds may be present in the pigment suspension. The further colorant compounds may comprise, for example, further inorganic pigments, organic pigments and/or direct-acting dyes.

As a second ingredient essential to the present disclosure, the pigment suspension comprises at least one $C_1$-$C_{10}$ alcohol.

The $C_1$-$C_{10}$ alcohol is preferably a $C_1$-$C_{10}$ aliphatic alcohol, which may be linear or branched and saturated or unsaturated.

Preferred $C_1$-$C_{10}$ alcohols are selected from the group of methanol, ethanol, 1-propanol, 2-propanol, 1-butanol, 2-butanol, 2-methylpropan-1-ol, 2-methylpropan-1-ol (tertButanol), 1-pentanol, 2-pentanol, 3-pentanol, 3-methylbutan-1-ol, 2-methylbutan-1-ol, 2,2-dimethylpropan-1-ol, 3-methylbutan-2-ol, 2-methylbutan-2-ol, 1-hexanol, 2-hexanol, 3-hexanol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2,3-dimethylbutan-1-ol, 3,3-dimethylbutan-1-ol, 2,3-dimethylbutan-2-ol, 3,3-dimethylbutan-2-ol, 2-ethylbutan-1-ol, 1-heptanol, 2-heptanol, 3-heptanol, 4-heptanol, 1-octanol, 2-octanol, 1-nonanol, 1-decanol, 2-methylhexan-2-ol, 2-methylheptan-2-ol, 3-methyl-3-pentanol, and mixtures thereof.

Of the $C_1$-$C_{10}$ alcohols, the pigment suspension preferably comprises at least one $C_1$-$C_{10}$ alcohol selected from the group of methanol, ethanol, 1-propanol, 2-propanol, 1-butanol, 2-butanol, 2-methylpropan-1-ol, 2-methylpropan-1-ol (tert-butanol) and mixtures thereof.

In a highly preferred embodiment, the pigment suspension is wherein the pigment suspension comprises at least one $C_1$-$C_{10}$ alcohol selected from the group of ethanol, 2-propanol and mixtures thereof.

Particularly stable pigment suspensions could be obtained if the pigment suspension comprises—based on the total weight of the pigment suspension—one or more $C_1$-$C_{10}$ alcohols in a total amount of from about 1 to about 80% by weight, preferably from about 5 to about 60% by weight and very preferably from about 10 to about 40% by weight.

As a third ingredient essential to the present disclosure, the pigment suspension comprises at least one diol.

A diol is a chemical compound with two hydroxyl groups (—OH groups). An aliphatic diol is also known as a glycol.

Preferred diols are $C_2$-$C_9$ alkanols with two hydroxyl groups and polyethylene glycols with 3 to 20 ethylene oxide units. The pigment suspension comprises at least one $C_2$-$C_9$ alkanol with two hydroxyl groups or at least one water-soluble polyethylene glycol with 3 to 20 ethylene oxide units or mixtures of at least one $C_2$-$C_9$ alkanol with two hydroxyl groups and at least one water-soluble polyethylene glycol with 3 to 20 ethylene oxide units.

Preferably, the $C_2$-$C_9$ alkanols with two hydroxyl groups are selected from ethylene glycol, 1,2-propylene glycol, 1,3-propylene glycol, 2-methyl-1,3-propanediol, 1,2-butylene glycol, 1,3-butylene glycol, 1,4-butylene glycol, 1,2-pentanediol, 1,5-pentanediol, 1,2-hexanediol, 1,6-hexanediol, 1,2-octanediol, 1,8-octanediol, cis-1,4-dimethylolcyclohexane, trans-1,4-dimethylolcyclohexane, any isomeric mixtures of cis- and trans-1,4-dimethylolcyclohexane, and mixtures of these diols. Also suitable diols are diethylene glycol, dipropylene glycol and/or PPG-10 butanediol (INCI). Suitable water-soluble polyethylene glycols are selected from PEG-3, PEG-4, PEG-6, PEG-7, PEG-8, PEG-9, PEG-10, PEG-12, PEG-14, PEG-16, PEG-18 and PEG-20, and mixtures thereof.

Of the diols mentioned, the pigment suspension preferably comprises at least one diol selected from the group of ethylene glycol, 1,2-propylene glycol, 1,3-propylene glycol, 1,2-butylene glycol, 1,3-butylene glycol, 1,4-butylene glycol, 1,2-pentanediol, 1,5-pentanediol, 1,2-hexanediol, 1,6-hexanediol, PEG-8, PEG-32 and PPG-10 butanediol (INCI).

In a highly preferred embodiment, the pigment suspension is wherein the pigment suspension comprises at least one diol selected from the group of ethylene glycol, 1,2-propylene glycol and 1,3-propylene glycol.

Particularly stable pigment suspensions could be obtained if the pigment suspension—based on the total weight of the pigment suspension—comprises one or more diols in a total amount of from about 1 to about 50% by weight, preferably from about 1 to about 40% by weight, more preferably from about 1 to about 30% by weight and very particularly preferably from about 1 to about 20% by weight.

As a fourth ingredient essential to the present disclosure, the pigment suspension comprises at least one thickening agent.

Suitable thickeners include, in particular, chemically modified celluloses, such as propyl cellulose, methyl ethyl cellulose, carboxymethyl cellulose, hydroxyethyl cellulose, methyl hydroxyethyl cellulose, ethyl hydroxyethyl cellulose, hydroxypropyl cellulose, Hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoetylcellulose, methylethylhydroxyethylcellulose, methlylsulfoethylcellulose and/or ethylsulfoethylcellulose.

In a preferred embodiment, a pigment suspension is wherein the pigment suspension comprises a thickening agent selected from the group of propyl cellulose, methyl ethyl cellulose, carboxymethyl cellulose, hydroxyethyl cellulose, methyl hydroxyethyl cellulose, ethyl hydroxyethyl cellulose, Hydroxypropylcellulose, hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoethylcellulose, methylethylhydroxyethylcellulose, methlylsulfoethylcellulose, ethylsulfoethylcellulose, and mixtures thereof.

Particularly suitable thickeners are selected from hydroxyethyl cellulose, hydroxypropyl cellulose, hydroxypropyl methyl cellulose and mixtures thereof.

In a particularly preferred embodiment, a pigment suspension is wherein the agent (a) and/or the agent (b) further comprises a thickening agent selected from the group of hydroxyethylcellulose, hydroxypropylcellulose, hydroxypropylmethylcellulose and mixtures thereof.

The amount of thickener is preferably between about 0.1 and about 10% by weight and more preferably between about 0.25 and about 5% by weight, in each case based on the total amount of pigment suspension.

As the fifth ingredient essential to the present disclosure, the pigment suspension comprises water. The amount of water is preferably from about 1 to about 50% by weight, preferably from about 1 to about 40% by weight, further preferably from about 1 to about 30% by weight and most preferably from about 1 to about 20% by weight, in each case based on the total amount of pigment suspension.

It has been shown that the pigments, especially those with substrate platelets of natural mica or synthetic mica, can be stably stored and accurately metered using the pigment suspension.

A second object of the present disclosure relates to a method for coloring keratinous material, in particular human hair, comprising the following steps:
Application of an agent (a) to the keratinous material, wherein the agent (a) comprises: (a1) at least one organic $C_1$-$C_6$-alkoxysilane, and
Application of an agent (b) to the keratinous material, wherein the agent (b) comprises: (b1) at least one sealing reagent,
wherein at least one of (a) and (b) further comprises a pigment suspension according to any one of claims 1 to 6.

The method may comprise an agent (a) prepared by combining a pigment suspension according to the present disclosure with one or more organic $C_1$-$C_6$ alkoxysilanes (a1) and/or their condensation products.

Alternatively, the method may comprise an agent (b) prepared by combining a pigment suspension according to the present disclosure with one or more sealing reagents (b1).

The agent (a) used in the method is wherein it comprises one or more organic $C_1$-$C_6$ alkoxysilanes and/or their condensation products.

The organic $C_1$-$C_6$ alkoxysilane (s) are organic, non-polymeric silicon compounds, preferably selected from the group of silanes having one, two or three silicon atoms Organic silicon compounds, alternatively referred to as organosilicon compounds, are compounds that either have a direct silicon-carbon (Si—C) bond or in which the carbon is attached to the silicon atom via an oxygen, nitrogen or sulfur atom. The organic silicon compounds of the present disclosure are preferably compounds comprising one to three silicon atoms. Particularly preferably, the organic silicon compounds contain one or two silicon atoms.

According to IUPAC rules, the term silane stands for a group of substances of chemical compounds based on a silicon structure and hydrogen. In organic silanes, the hydrogen atoms are wholly or partially replaced by organic groups such as (substituted) alkyl groups and/or alkoxy groups.

A characteristic feature of the $C_1$-$C_6$ alkoxysilanes is that at least one $C_1$-$C_6$ alkoxy group is directly bonded to a silicon atom. The $C_1$-$C_6$ alkoxysilanes as contemplated herein thus comprise at least one structural unit R'R''R'''Si—O—($C_1$-$C_6$ alkyl) where the radicals R', R'' and R''' represent the three remaining bond valencies of the silicon atom.

The $C_1$-$C_6$ alkoxy group or groups bonded to the silicon atom are very reactive and are hydrolyzed at high rates in the presence of water, the reaction rate depending, among other things, on the number of hydrolyzable groups per molecule. If the hydrolysable $C_1$-$C_6$ alkoxy group is an ethoxy group, the organic silicon compound preferably comprises a structural unit R'R''R'''Si—O—CH2-CH3. The R', R'', and R''' radicals again represent the three remaining free valences of the silicon atom.

Even the addition of small amounts of water leads first to hydrolysis and then to a condensation reaction between the organic alkoxysilanes. For this reason, both the organic alkoxysilanes and their condensation products may be present in the agent.

A condensation product is a product formed by reaction of at least two organic $C_1$-$C_6$ alkoxysilanes with elimination of water and/or with elimination of a $C_1$-$C_6$ alkanol.

The condensation products can be, for example, dimers, but also trimers or oligomers, with the condensation products being in equilibrium with the monomers.

Depending on the amount of water used or consumed in the hydrolysis, the equilibrium shifts from monomeric $C_1$-$C_6$ alkoxysilane to condensation product.

In a very particularly preferred embodiment, a method is wherein the agent (a) comprises one or more organic $C_1$-$C_6$ alkoxysilanes selected from silanes having one, two or three silicon atoms, the organic silicon compound further comprising one or more basic chemical functions.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

A very particularly preferred agent (a), which can be used in the method, is wherein the cosmetic agent comprises one or more organic $C_1$-$C_6$ alkoxysilanes selected from the group of silanes having one, two or three silicon atoms, and wherein the $C_1$-$C_6$ alkoxysilanes further comprise one or more basic chemical functions.

Particularly good results were obtained when $C_1$-$C_6$ alkoxysilanes of the formula (S-I) and/or (S-II) and/or (S-IV) were used in the agent (a). Since, as previously described, hydrolysis/condensation already starts at traces of moisture, the condensation products of the $C_1$-$C_6$ alkoxysilanes of formula (S-I) and/or (S-II) and/or (S-IV) are also included in this embodiment.

In another very particularly preferred embodiment, a method is wherein the agent (a) comprises one or more organic $C_1$-$C_6$ alkoxysilanes of the formula (S-I) and/or (S-II),

$$R_1R_2N\text{-}L\text{-}Si(OR_3)_a(R_4)_b \quad (S\text{-}I)$$

where
$R_1$, $R_2$ independently represent a hydrogen atom or a $C_1$-$C_6$ alkyl group,
L is a linear or branched, divalent $C_1$-$C_{20}$ alkylene group,
$R_3$, $R_4$ are independent of each other for a $C_1$-$C_6$ alkyl group,
a, represents an integer from 1 to 3, and
b is the integer 3-a, and

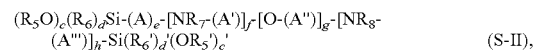

$$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (S\text{-}II),$$

where
R5, R5', R5", R6, R6' and R6" independently represent a $C_1$-$C_6$ alkyl group,
A, A', A", A'" and A"" independently represent a linear or branched $C_1$-$C_{20}$ divalent alkylene group,
$R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (S-III), $$(A'''')-Si(R_6'')_{d''}(OR_5'')_{c''} \quad (S\text{-}III)$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
with the proviso that at least one of the radicals from e, f, g and h is different from 0,
and/or their condensation products.

The substituents $R_1$, $R_2$, $R_3$, $R_4$, $R_5$, $R_5'$, $R_5"$, $R_6$, $R_6'$, $R_6"$, $R_7$, $R_8$, L, A, A', A", A'" and A"" in the compounds of formula (S-I) and (S-II) are exemplified below:

Examples of a $C_1$-$C_6$ alkyl group include methyl, ethyl, propyl, isopropyl, n-butyl, s-butyl and t-butyl, n-pentyl and n-hexyl groups. Propyl, ethyl and methyl are preferred alkyl radicals. Examples of a $C_2$-$C_6$ alkenyl group are vinyl, allyl, but-2-enyl, but-3-enyl as well as isobutenyl, preferred $C_2$-$C_6$ alkenyl radicals are vinyl and allyl. Preferred examples of a hydroxy-$C_1$-$C_6$-alkyl group include a hydroxymethyl, a 2-hydroxyethyl, a 2-hydroxypropyl, a 3-hydroxypropyl, a 4-hydroxybutyl, a 5-hydroxypentyl and a 6-hydroxyhexyl group; a 2-hydroxyethyl group is particularly preferred. Examples of an amino-$C_1$-$C_6$-alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched $C_3$-$C_{20}$ divalent alkylene groups are (—$CH_2$—CH($CH_3$)—) and (—$CH_2$—CH($CH_3$)—$CH_2$—).

In the organic silicon compounds of the formula (S-I)

$$R_1R_2N\text{-}L\text{-}Si(OR_3)_a(R_4)_b \quad (S\text{-}I),$$

$R_1$ and $R_2$ independently represent a hydrogen atom or a $C_1$-$C_6$ alkyl group. Very preferably, $R_1$ and $R_2$ both represent a hydrogen atom.

In the middle part of the organic silicon compound is the structural unit or linker -L- which stands for a linear or branched, divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each -L- grouping may form two bonds.

Preferably, -L- represents a linear, divalent $C_1$-$C_{20}$ alkylene group. Further preferably, -L- represents a linear divalent $C_1$-$C_6$ alkylene group. Particularly preferably, -L- stands for a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very preferably, L represents a propylene group (—$CH_2$—$CH_2$—$CH_2$—).

The alkoxysilanes of the formula (S-I)

$$R_1R_2N\text{-}L\text{-}Si(OR_3)_a(R_4)_b \quad (S\text{-}I),$$

carry the silicon-containing grouping —$Si(OR_3)_a(R_4)_b$ at one end.

In the terminal structural unit —$Si(OR_3)_a(R_4)_b$, R3 and R4 independently represent a $C_1$-$C_6$ alkyl group, Particularly preferably, $R_3$ and $R_4$ independently represent a methyl group or an ethyl group.

Here, a represents an integer from 1 to 3, and b represents the integer 3-a. If a represents number 3, then b is 0. If a stands for number 2, then b is equal to 1. If a stands for number 1, then b is equal to 2.

Agent (a) with particularly good dyeing properties for keratinous materials could be prepared if the agent (a) comprises at least one organic $C_1$-$C_6$-alkoxysilane of the formula (S-I) in which the radicals $R_3$, $R_4$ independently of one another represent a methyl group or an ethyl group.

Furthermore, dyeings with the best color fastness could be obtained if the agent (a) comprises at least one organic $C_1$-$C_6$-alkoxysilane of the formula (S-I) in which the radical a represents number 3. In this case, the radical b stands for number 0.

In a further preferred embodiment, the agent (a) is wherein it comprises one or more organic $C_1$-$C_6$ alkoxysilanes of the formula (S-I),
where
$R_3$, $R_4$ independently represent a methyl group or an ethyl group, and
a stands for number 3 and
b stands for number 0.

In a further preferred embodiment, a method as contemplated herein is wherein the agent (a) comprises at least one or more organic $C_1$-$C_6$ alkoxysilanes of the formula (S-I), $$R_1R_2N\text{-}L\text{-}Si(OR_3)_a(R_4)_b \quad (S\text{-}I),$$

where
$R_1$, $R_2$ both represent a hydrogen atom, and
L is a linear, divalent $C_1$-$C_6$ alkylene group, preferably a propylene group (—$CH_2$—$CH_2$—$CH_2$—) or an ethylene group (—$CH_2$—$CH_2$—),
$R_3$ represents an ethyl group or a methyl group,
$R_4$ represents a methyl group or an ethyl group,
a stands for number 3 and
b stands for number 0.

Particularly well suited organic silicon compounds of formula (I) are

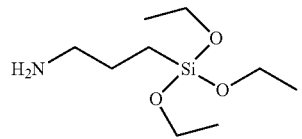

(3-Aminopropyl)triethoxysilane

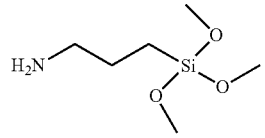

(3-Aminopropyl)trimethoxysilane

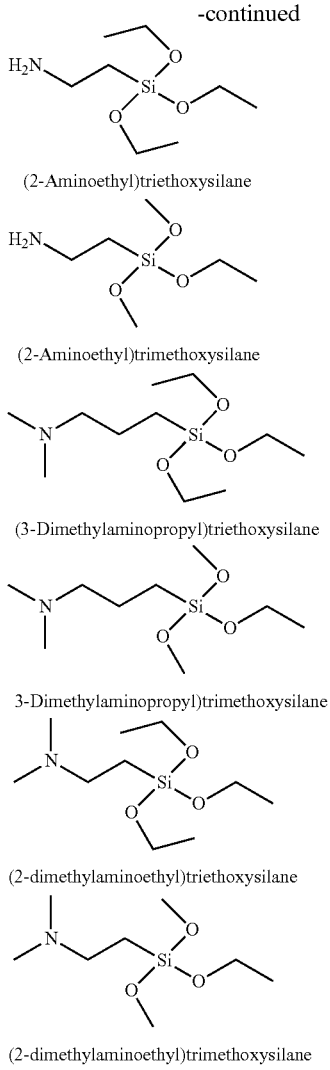

(2-Aminoethyl)triethoxysilane (2-Aminoethyl)trimethoxysilane (3-Dimethylaminopropyl)triethoxysilane 3-Dimethylaminopropyl)trimethoxysilane (2-dimethylaminoethyl)triethoxysilane (2-dimethylaminoethyl)trimethoxysilane  and/or In a further preferred embodiment, a method as contemplated herein is wherein the agent (a) comprises at least one organic $C_1$-$C_6$ alkoxysilane of the formula (S-I) selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-dimethylaminoethyl)triethoxysilane,
(2-Dimethylaminoethyl)trimethoxysilane
and/or their condensation products.

The aforementioned organic silicon compounds of formula (I) are commercially available.
(3-Aminopropyl)trimethoxysilane is available for purchase from Sigma-Aldrich, for example.
(3-Aminopropyl)triethoxysilane is also commercially available from Sigma-Aldrich.

In a further embodiment of the method as contemplated herein, agent (a) may also comprise one or more organic $C_1$-$C_6$ alkoxysilanes of the formula (S-II),

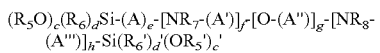  (S-II).

The alkoxysilanes of the formula (S-II) each carry at their two ends the silicon-containing groupings $(R_5O)_c(R_6)_dSi$— and —$Si(R_6')_{d'}(OR_5')_{c'}$.

In the middle part of the molecule of formula (S-II) there are the groupings -(A)$_e$- and —[NR$_7$-(A')]$_f$- and —[O-(A'')]$_g$- and —[NR$_8$-(A''')]$_h$-. Here, each of the radicals e, f, g and h can independently represent number 0 or 1, with the proviso that at least one of the radicals e, f, g and h is other than 0. In other words, a preferred alkoxysilane of formula (II) comprises at least one moiety selected from the group of -(A)- and —[NR$_7$-(A')]- and —[O-(A'')]- and —[NR$_8$-(A''')]-.

In the two terminal structural units $(R_5O)_c(R_6)_dSi$— and —$Si(R_6')_{d'}(OR_5')_{c'}$, the radicals R5, R5', R5'' independently represent a $C_1$-$C_6$ alkyl group. The R6, R6' and R6'' radicals independently represent a $C_1$-$C_6$ alkyl group.

Here, c represents an integer from 1 to 3, and d represents the integer 3-c. If c stands for number 3, then d is 0. If c stands for the number 2, then d is equal to 1. If c stands for the number 1, then d is equal to 2.

Similarly, c' represents an integer from 1 to 3, and d' represents the integer 3-c'. If c' stands for number 3, then d' is equal to 0. If c' stands for number 2, then d' is equal to 1. If c' stands for number 1, then d' is equal to 2.

Colors with the best color fastness could be obtained when the radicals c and c' both stand for number 3. In this case, d and d' both stand for number 0.

In another preferred embodiment, a method is wherein the agent (a) comprises one or more organic $C_1$-$C_6$ alkoxysilanes of formula (S-II),

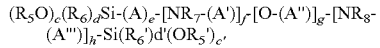  (S-II), where
R5 and R5' independently represent a methyl group or an ethyl group,
c and c' both stand for number 3 and
d and d' both stand for number 0.

When c and c' are both 3 and d and d' are both 0, the organic silicon compounds as contemplated herein correspond to the formula (S-IIa)

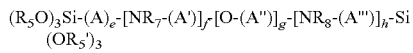  (S-IIa).

The radicals e, f, g, and h can independently represent number 0 or 1, with at least one residue from e, f, g, and h being different from zero. The abbreviations e, f, g and h thus define which of the groupings -(A)$_e$- and —[NR$_7$-(A')]$_f$- and —[O-(A'')]$_g$- and —[NR$_8$-(A''')]$_h$- are located in the middle part of the organic silicon compound of formula (II).

In this context, the presence of certain groupings has proven to be particularly advantageous in terms of achieving colorfast dyeing results. Particularly good results could be obtained if at least two of the radicals e, f, g and h stand for number 1. Very preferably, e and f both stand for the number 1. Furthermore, g and h both represent number 0.

When e and f are both 1 and g and h are both 0, the organic silicon compounds as contemplated herein are represented by the formula (S-IIb)

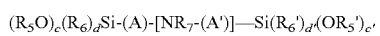  (S-IIb).

Radicals A, A', A'', A''' and A'''' independently represent a linear or branched $C_1$-$C_{20}$ divalent alkylene group. Preferably, A, A', A'', A''' and A'''' independently represent a linear divalent $C_1$-$C_{20}$ alkylene group. Further preferably, A, A', A'', A''' and A'''' independently represent a linear divalent $C_1$-$C_6$ alkylene group.

The divalent $C_1$-$C_{20}$ alkylene group may alternatively be referred to as a divalent or divalent $C_1$-$C_{20}$ alkylene group, by which is meant that each grouping A, A', A", A'" and A"" may form two bonds.

Particularly preferably, the radicals A, A', A", A'" and A"" independently represent a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very preferably, the radicals A, A', A", A'" and A"" represent a propylene group (—$CH_2$—$CH_2$—$CH_2$—).

When the radical f represents number 1, the organic silicon compound of formula (II) comprises a structural grouping —[$NR_7$-(A')]-.

When the radical h represents number 1, the organic silicon compound of formula (II) comprises a structural grouping —[$NR_8$-(A'")]-.

Here, $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (S-III)

$$-(A"")-Si(R_6")_{d"}(OR_5")_{c"} \quad (S\text{-}III).$$

Very preferably, $R_7$ and $R_8$ independently represent a hydrogen atom, a methyl group, a 2-hydroxyethyl group, a 2-alkenyl group, a 2-aminoethyl group or a group of formula (S-III).

When the radical f represents number 1 and the radical h represents number 0, the organic silicon compound as contemplated herein comprises the grouping [$NR_7$-(A')] but not the grouping —[$NR_8$-(A'")]. If the radical R7 now stands for a grouping of the formula (III), the organic silicon compound comprises 3 reactive silane groups.

In another preferred embodiment, a method is wherein the agent (a) comprises one or more organic $C_1$-$C_6$ alkoxysilanes of formula (S-II)

$$(R_5O)c(R_6)_dSi\text{-}(A)_e\text{-}[NR_7\text{-}(A')]_f\text{-}[O\text{-}(A")]_g\text{-}[NR_8\text{-}(A'")]_h\text{-}Si(R_6')_{d'}(OR_5')_{c'}, \quad (II),$$

where e and f both stand for number 1, g and h both stand for number 0,

A and A' independently of one another represent a linear, divalent $C_1$-$C_6$ alkylene group and $R_7$ represents a hydrogen atom, a methyl group, a 2-hydroxyethyl group, a 2-alkenyl group, a 2-aminoethyl group or a group of the formula (S-III).

In another preferred embodiment, a method is wherein agent (a) comprises one or more organic $C_1$-$C_6$ alkoxysilanes of the formula (S-II), wherein e and f both stand for number 1, g and h both stand for number 0, A and A' independently represent a methylene group (—$CH_2$—), an ethylene group (—$CH_2$—$CH_2$—) or a propylene group (—$CH_2$—$CH_2$—$CH_2$), and $R_7$ represents a hydrogen atom, a methyl group, a 2-hydroxyethyl group, a 2-alkenyl group, a 2-aminoethyl group or a group of the formula (S-III).

Well-suited organic silicon compounds of the formula (S-II) are

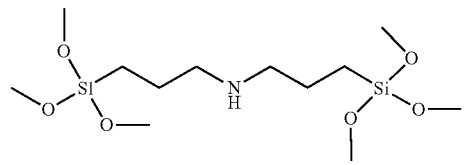

3-(Trimethoxysilyl)-N-[3-(trimethoxysilyl)propyl]-1-propanamine

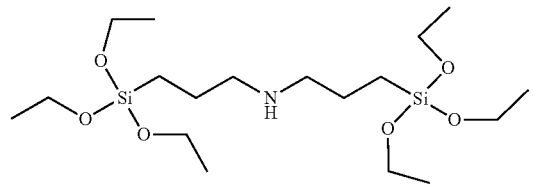

3-(Triethoxysilyl)-N-[3-(triethoxysilyl)propyl]-1-propanamine

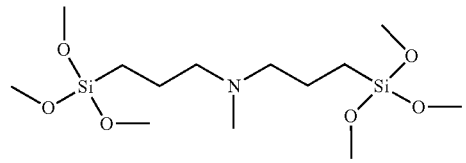

N-methyl-3-(trimethoxysilyl)-N-[3(trimethoxysilyl)propyl]-1-propanamine

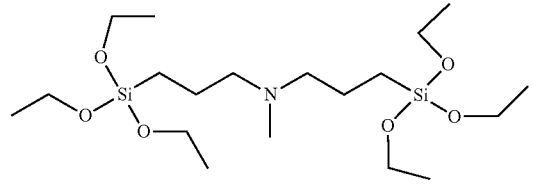

N-methyl-3-(triethoxysilyl)-N-[3-(triethoxysilyl)propyl]-1-propanamine

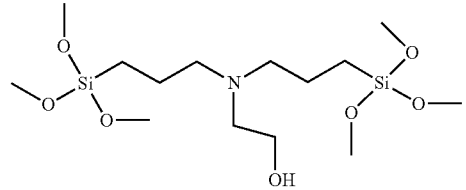

2-[Bis[3-(trimethoxysilyl)propyl]amino]ethanol

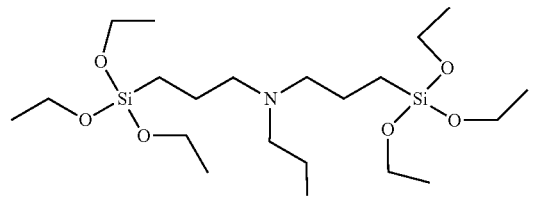

2-[Bis[3-(triethoxysilyl)propyl]amino]ethanol

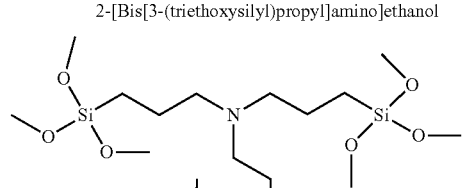

3-(Trimethoxysilyl)-N,N-bis[3-(trimethoxysilyl)propyl]-1-propanamine

-continued

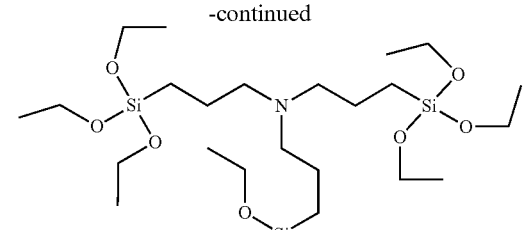
3-(Triethoxysilyl)-N,N-bis[3-(triethoxysilyl)propyl]-1-propanamine

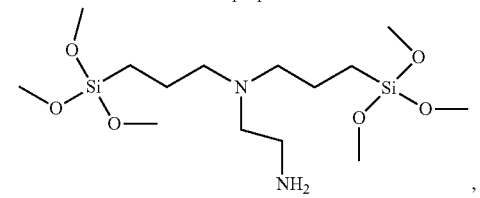
N1,N1-bis[3-(trimethoxysilyl)propyl]-1,2-ethanediamine

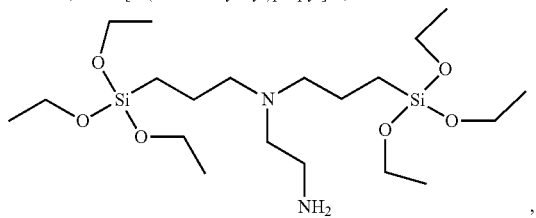
N1,N1-bis[3-(triethoxysilyl)propyl]-1,2-ethanediamine

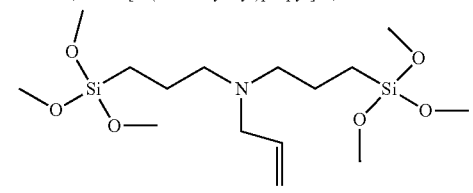
N,N-bis[3-(trimethoxysilyl)propyl]-2-propen-1-amine

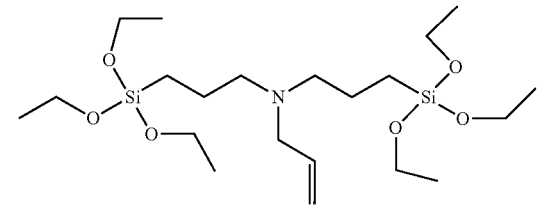
N,N-bis[3-(triethoxysilyl)propyl]-2-propen-1-amine

The aforementioned organic silicon compounds of formula (S-II) are commercially available.

Bis(trimethoxysilylpropyl)amines with the CAS number 82985-35-1 can be purchased from for example, can be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively known as bis(3-trimethoxysilylpropyl)-N-methylamine and can be purchased commercially from Sigma-Aldrich or Fluorochem.

3-(Triethoxysilyl)-N,N-bis[3-(triethoxysilyl)propyl]-1-propanamine with CAS number 18784-74-2 can be purchased from Fluorochem or Sigma-Aldrich, for example.

In another preferred embodiment, a method is wherein the agent (a) comprises one or more organic $C_1$-$C_6$ alkoxysilanes of formula (S-II) selected from the group of 3-(Trimethoxysilyl)-N-[3-(trimethoxysilyl)propyl]-1-propanamine 3-(Triethoxysilyl)-N-[3-(triethoxysilyl)propyl]-1-propanamine N-methyl-3-(trimethoxysilyl)-N-[3-(trimethoxysilyl)propyl]-1-propanamine N-methyl-3-(triethoxysilyl)-N-[3-(triethoxysilyl)propyl]-1-propanamine 2-[Bis[3-(trimethoxysilyl)propyl]amino]ethanol 2-[Bis[3-(triethoxysilyl)propyl]amino]ethanol 3-(Trimethoxysilyl)-N,N-bis[3-(trimethoxysilyl)propyl]-1-propanamine 3-(triethoxysilyl)-N,N-bis[3-(triethoxysilyl)propyl]-1-propanamine N1,N1-bis[3-(trimethoxysilyl)propyl]-1,2-ethanediamine, N1,N1-bis[3-(triethoxysilyl)propyl]-1,2-ethanediamine, N,N-bis[3-(trimethoxysilyl)propyl]-2-propen-1-amine and/or N,N-bis[3-(triethoxysilyl)propyl]-2-propen-1-amine, and/or their condensation products.

In dyeing trials, it has also been found to be particularly advantageous if the agent (a) used in the method comprises at least one organic $C_1$-$C_6$-alkoxysilane of the formula (S-IV)

$$R_9Si(OR_{10})_k(R_{11})_m \quad \text{(S-IV)}.$$

The compounds of formula (S-IV) are organic silicon compounds selected from silanes having one, two or three silicon atoms, wherein the organic silicon compound comprises one or more hydrolyzable groups per molecule.

The organic silicon compound(s) of formula (S-IV) may also be referred to as silanes of the alkyl-$C_1$-$C_6$ alkoxysilane type, $$R_9Si(OR_{10})_k(R_{11})_m \quad \text{(S-IV)},$$

where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k.

In a further embodiment, a method is wherein the agent (a) comprises one or more organic $C_1$-$C_6$ alkoxysilanes of formula (S-IV), $$R_9Si(OR_{10})_k(R_{11})_m \quad \text{(S-IV)},$$

where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k,
and/or their condensation products.

In the organic $C_1$-$C_6$ alkoxysilanes of the formula (S-IV), the radical $R_9$ represents a $C_1$-$C_{12}$ alkyl group. This $C_1$-$C_{12}$ alkyl group is saturated and can be linear or branched. Preferably, $R_9$ represents a linear $C_1$-$C_8$ alkyl group. Preferably, $R_9$ represents a methyl group, an ethyl group, an n-propyl group, an n-butyl group, an n-pentyl group, an n-hexyl group, an n-octyl group, or an n-dodecyl group. Particularly preferably, $R_9$ represents a methyl group, an ethyl group or an n-octyl group.

In the alkoxysilanes of the formula (S-IV), the radical $R_{10}$ represents a $C_1$-$C_6$ alkyl group. Particularly preferably, $R_{10}$ represents a methyl group or an ethyl group.

In the alkoxysilanes of the formula (S-IV), the radical $R_{11}$ represents a $C_1$-$C_6$ alkyl group. Particularly preferably, $R_{11}$ represents a methyl group or an ethyl group.

Furthermore, k stands for an integer from 1 to 3, and m stands for the integer 3-k. If k stands for number 3, then m is 0. If k stands for number 2, then m is equal to 1. If k stands for number 1, then m is equal to 2.

Colorations with the best color fastness could be obtained if the cosmetic agent comprises at least one organic $C_1$-$C_6$ alkoxysilane of the formula (S-IV) in which the radical k represents number 3. In this case, the radical m stands for number 0.

Particularly suitable organic silicon compounds of the formula (S-IV) are

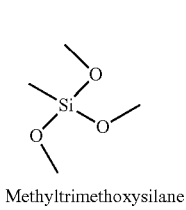
Methyltrimethoxysilane

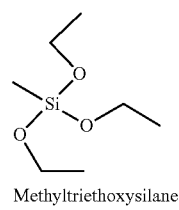
Methyltriethoxysilane

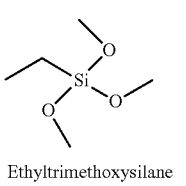
Ethyltrimethoxysilane

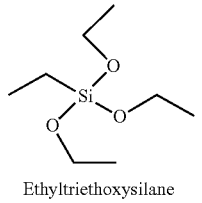
Ethyltriethoxysilane

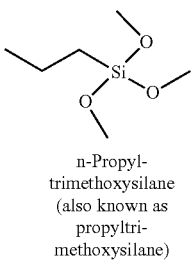
n-Propyl-trimethoxysilane
(also known as propyltri-methoxysilane)

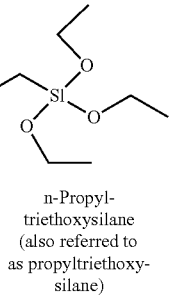
n-Propyl-triethoxysilane
(also referred to as propyltriethoxy-silane)

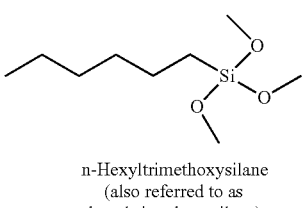
n-Hexyltrimethoxysilane
(also referred to as hexyltrimethoxysilane)

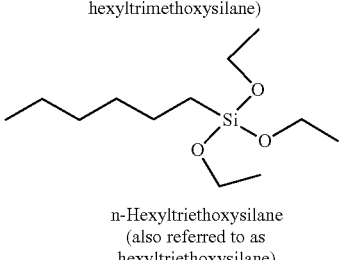
n-Hexyltriethoxysilane
(also referred to as hexyltriethoxysilane)

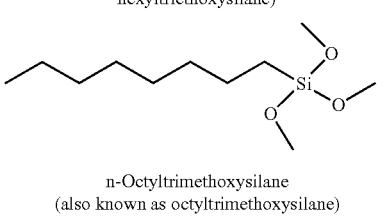
n-Octyltrimethoxysilane
(also known as octyltrimethoxysilane)

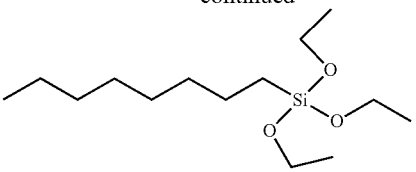
n-Octyltriethoxysilane
(also referred to as octyltriethoxysilane)

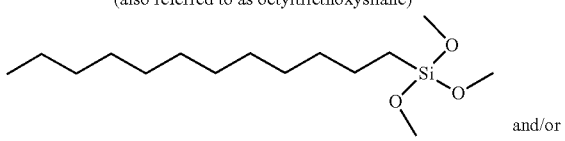
n-Dodecyltrimethoxysilane
(also referred to as dodecyltrimethoxysilane)

and/or

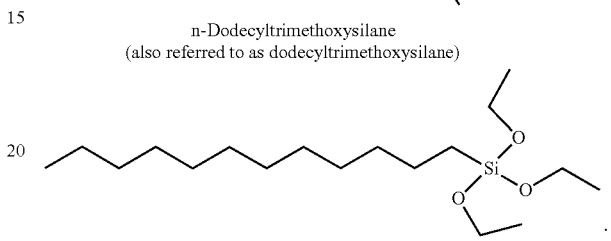
n-Dodecyltriethoxysilane (also known as dodecyltriethoxysilane) and octadecyltrimethoxysilane and/or octadecyltriethoxysilane In another preferred embodiment, a method is wherein the agent (a) comprises at least one $C_1$-$C_6$ organic alkoxysilane of formula (S-IV) selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane,
Octadecyltrimethoxysilane,
Octadecyltriethoxysilane,
their mixtures
and/or their condensation products.

It has been found that, with regard to coloring keratinous material, it is particularly preferable if the cosmetic agent comprises two alkoxysilanes that are structurally different from each other.

In a preferred embodiment, a method is wherein the agent (a) comprises at least one alkoxysilane of formula (S-I) and at least one alkoxysilane of formula (S-IV).

The corresponding hydrolysis or condensation products are, for example, the following compounds:

Hydrolysis of $C_1$-$C_6$ alkoxysilane of formula (S-I) with water (reaction scheme using 3-aminopropyltriethoxysilane as an example):

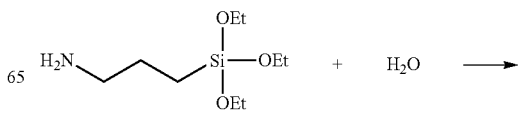

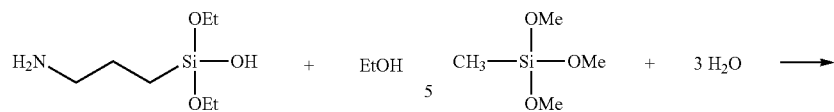

Depending on the amount of water used, the hydrolysis reaction can also take place several times per $C_1$-$C_6$ alkoxysilane used:

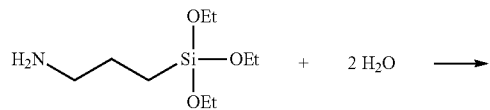

respectively

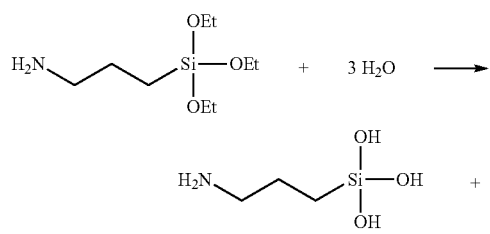

Hydrolysis of $C_1$-$C_6$ alkoxysilane of the formula (S-IV) with water (reaction scheme using methyltrimethoxysilane as an example):

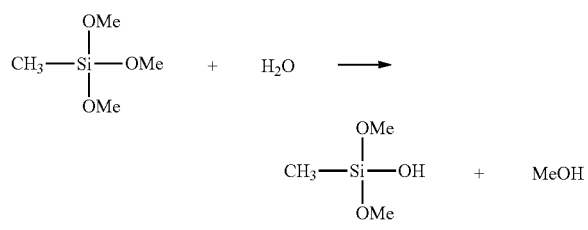

Depending on the amount of water used, the hydrolysis reaction can also take place several times per $C_1$-$C_6$ alkoxysilane used:

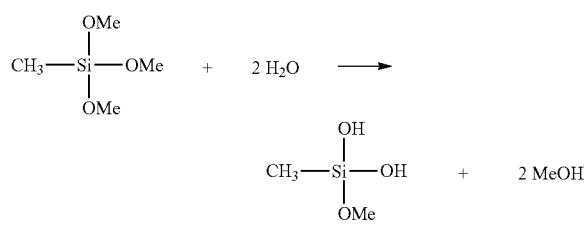

respectively

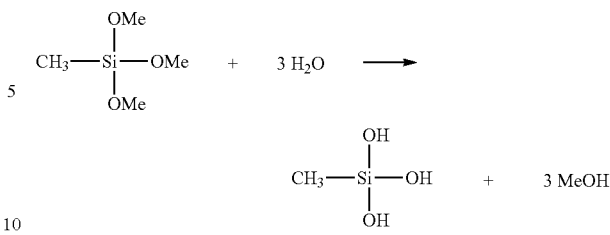

Possible condensation reactions include (shown using the mixture (3-aminopropyl)triethoxysilane and methyltrimethoxysilane):

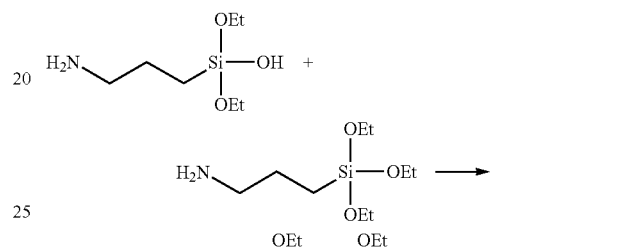

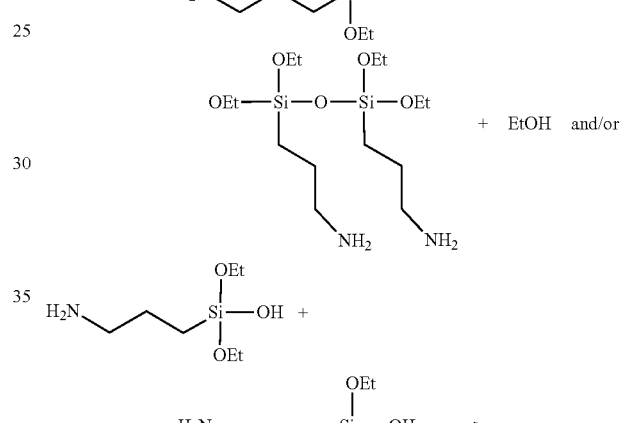

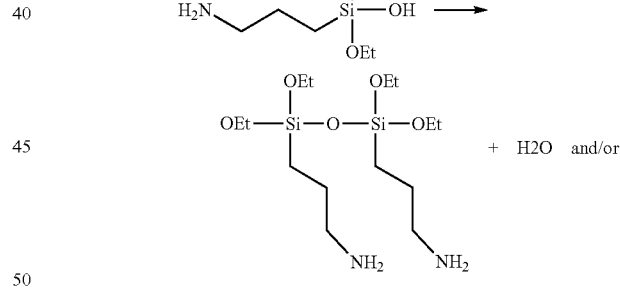

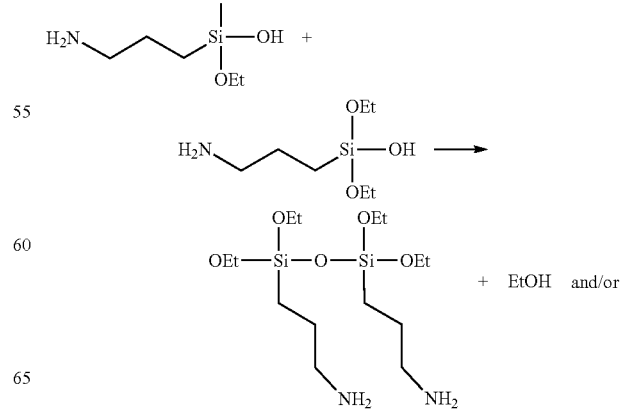

-continued

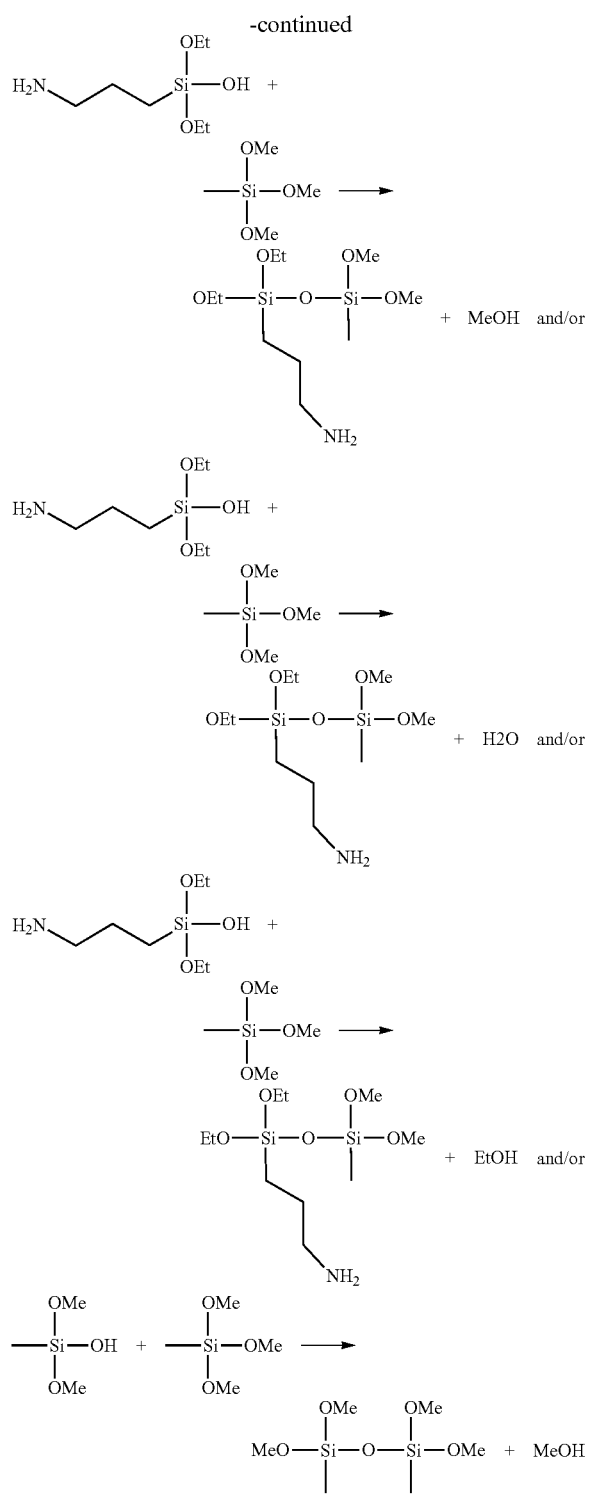

In the above exemplary reaction schemes the condensation to a dimer is shown in each case, but further condensations to oligomers with several silane atoms are also possible and also preferred.

Both partially hydrolyzed and fully hydrolyzed $C_1$-$C_6$ alkoxysilanes of the formula (S-I) can participate in these condensation reactions, which undergo condensation with as yet unreacted, partially or also fully hydrolyzed $C_1$-$C_6$ alkoxysilanes of the formula (S-I). In this case, the $C_1$-$C_6$ alkoxysilanes of formula (S-I) react with themselves.

Furthermore, both partially hydrolyzed and fully hydrolyzed $C_1$-$C_6$-alkoxysilanes of the formula (S-I) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-I) react with the $C_1$-$C_6$ alkoxysilanes of formula (S-IV).

Furthermore, both partially hydrolyzed and fully hydrolyzed $C_1$-$C_6$ alkoxysilanes of the formula (S-IV) can also participate in the condensation reactions, which undergo condensation with as yet unreacted, partially or also fully hydrolyzed $C_1$-$C_6$ alkoxysilanes of the formula (S-IV). In this case, the $C_1$-$C_6$ alkoxysilanes of formula (S-IV) react with themselves.

Agent (a) may contain one or more organic $C_1$-$C_6$ alkoxysilanes in various proportions. This is determined by the expert depending on the desired application. In the case of coloring keratinous material, for example, the amount may depend on the thickness of the silane coating on the keratinous material and the amount of keratinous material to be treated.

Particularly storage-stable agents (a) with very good coloring results when applied to keratinous material could be obtained if the cosmetic agent comprises—based on its total weight—one or more organic $C_1$-$C_6$-alkoxysilanes and/or the condensation products thereof in a total amount of from about 30 to about 85% by weight, preferably from about 35 to about 80% by weight, more preferably from about 40 to about 75% by weight, still more preferably from about 45 to about 70% by weight and very particularly preferably from about 50 to about 65% by weight.

It may be preferred that the ready-to-use agent (a) comprises further ingredients in addition to the pigment suspension as contemplated herein and the organic $C_1$-$C_6$ alkoxysilane(s).

The cosmetic product comprises alkoxysilanes, a class of highly reactive compounds that can undergo hydrolysis or oligomerization and/or polymerization when used.

To avoid premature oligomerization or polymerization, it can be of considerable advantage to the user to prepare the ready-to-use cosmetic product just before application.

To avoid premature oligomerization or polymerization, it is of considerable advantage to the user to prepare the ready-to-use agent (a) only shortly before application.

For example, the user can stir or shake an agent (a') comprising the alkoxysilanes (a1) with an agent (a") comprising the pigment suspension as contemplated herein. The user can apply this mixture of (a') and (a") either immediately after its preparation or after a short reaction time of about 10 seconds to about 20 minutes—to the keratinous materials. Subsequently, the user can apply the agent (b).

The method of dyeing keratinous material includes, in addition to the application of agent (a), the application of agent (b). The agent (b) is wherein it comprises at least one sealing reagent (b1).

Agent (b) is a post-treatment agent and the application of agent (b) to the keratinous material treated with agent (a) has the effect of making the colorations obtained in the process more durable. In particular, the use of agent (b) can improve the color fastness and the rub fastness of the dyeings obtained in the process.

It is preferred that the sealing reagent (b1) comprises a compound selected from the group of film-forming polymers, alkalizing agents, acidifying agents, and mixtures thereof.

In the case that the agent (b) comprises the pigment suspension as contemplated herein, it may also be preferred to prepare the ready-to-use agent (b) by mixing two agents (b') and (b"). In this embodiment, the agent (b') comprises the sealing reagent (b1) and the agent (b") comprises the pigment suspension.

To increase user convenience, the user is preferably provided with all the necessary means in the form of a multi-component packaging unit (kit-of-parts).

A third object of the present disclosure is therefore a multi-component packaging unit (kit-of-parts) for dyeing keratinous material, comprising separately prepared
a first container comprising an agent (a'), wherein the agent comprises (a'):
(a1) at least one or more $C_1$-$C_6$ organic alkoxysilanes,
a second container comprising an agent (a"), wherein the agent comprises (a"):
(a2) a pigment suspension as contemplated herein, and
a third container comprising an agent (b"), said agent comprising (b"):
(b1) a sealing reagent.

A fourth object of the present disclosure is therefore a multi-component packaging unit (kit-of-parts) for dyeing keratinous material, comprising separately prepared
a first container comprising an agent (a), wherein the agent comprises (a):
(a1) at least one or more $C_1$-$C_6$ organic alkoxysilanes,
a second container comprising an agent (b'), wherein the agent comprises (b'):
(b1) a sealing reagent, and
a third container comprising an agent (b"), said agent comprising (b"):
(b2) a pigment suspension as contemplated herein.

With regard to further preferred embodiments of the multi-component packaging units (kit-of-parts), what has been said about the pigment suspensions and/or processes applies mutatis mutandis.

EXAMPLE 1

The following formulations were prepared (unless otherwise stated, all figures are in % by weight of active substance)

| Agent (a) | Weight % |
|---|---|
| (3-Aminopropyl)triethoxysilane | 20 |
| Methyltriethoxysilane | 70 |
| Water | ad 100 |

| Agent (b') | Weight % |
|---|---|
| Ethylene/Sodium Acrylate Copolymer (b1) (25% solution) | 15 |
| Water | ad 100 |

| Pigment suspension | Weight % |
|---|---|
| Timiron SynWhite Satin (ex Merck) | 45 |
| 1,2-Propanol | 12 |
| 2-Propanol | 30 |
| Hydroxypropylmethylcellulose | 1 |
| Water | ad 100 |

The ready-to-use agent (b) was prepared by mixing 60 g of the agent (b') and 40 g of the pigment suspension.

The agent (a) was massaged into one strand of hair at a time (Kerling, Euronatural hair white), and left to act for 1 minute. The agent (a) was then rinsed with water.

Subsequently, agent (b) was applied to the hair strand, left to act for 5 minutes and then also rinsed with water.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A pigment suspension comprising:
a) at least one colorant compound selected from the group of pigments, wherein the at least one colorant compound comprises a pigment with a synthetic fluorophlogopite mica substrate,
b) at least one $C_1$-$C_{10}$ alcohol,
c) at least one diol,
d) at least one thickening agent, and
e) water.
2. A pigment suspension according to claim 1, wherein the pigment comprises a substrate platelet, wherein the substrate platelet comprises a metal, a metal alloy, natural mica, synthetic mica, or glass.
3. A pigment suspension according to claim 1, wherein the at least one thickening agent is selected from the group of carboxymethyl cellulose, carboxymethylhydroxyethylcellulose, sulfoethylcellulose, carboxymethylsulfoethylcellulose, hydroxypropylsulfoethylcellulose, hydroxyethylsulfoethylcellulose, methlylsulfoethylcellulose, ethylsulfoethylcellulose, or mixtures thereof.
4. A pigment suspension according to claim 1, wherein the at least one C1-C10 alcohol is selected from the group of ethanol, 2-propanol, or mixtures thereof.
5. A pigment suspension according to claim 1, wherein the at least one diol is selected from the group of ethylene glycol, 1,2-propylene glycol, 1,3-propylene glycol, or mixtures thereof.
6. A pigment suspension according to claim 1, wherein the at least one thickening agent is selected from the group of propyl cellulose, methyl ethyl cellulose, carboxymethyl cellulose, hydroxyethyl cellulose, methyl hydroxyethyl cellulose, ethyl hydroxyethyl cellulose, hydroxypropyl cellulose, hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoethylcellulose, methylethylhydroxyethylcellulose, methlylsulfoethylcellulose, ethylsulfoethylcellulose, or mixtures thereof.
7. A method for dyeing keratinous material comprising the following steps:
applying an agent (a) to the keratinous material, wherein the agent (a) comprises:
(a1) at least one organic $C_1$-$C_6$-alkoxysilane, wherein the agent (a) comprises the at least one organic $C_1$-$C_6$-alkoxysilane in an amount of from about 50 to about 65 weight percent, based on a total weight of the agent (a), and
applying an agent (b) to the keratinous material, wherein the agent (b) comprises:

(b1) at least one sealing reagent,
wherein at least one of the agent (a) and the agent (b) further comprises a pigment suspension comprising;
  a) at least one colorant compound selected from the group of pigments,
  b) at least one $C_1$-$C_{10}$ alcohol,
  c) at least one diol,
  d) at least one thickening agent, and
  e) water.

8. The method for dyeing keratinous material according to claim 7, wherein the agent (a) comprises one or more organic $C_1$-$C_6$-alkoxysilanes of the formula (S-I) and/or (S-II) and/or (S-IV), $$R_1R_2N\text{-}L\text{-}Si(OR_3)_a(R_4)_b \quad \text{(S-I)}$$

where
$R_1$, $R_2$ independently represent a hydrogen atom or a $C_1$-$C_6$ alkyl group,
L is a linear or branched, divalent $C_1$-$C_{20}$ alkylene group,
$R_3$, $R_4$ are independent of each other for a $C_1$-$C_6$ alkyl group,
a, represents an integer from 1 to 3, and
b is the integer 3-a, and $$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad \text{(S-II)},$$

where
$R_5$, $R_{5'}$, $R_{5''}$, $R_6$, $R_{6'}$ and $R_6'$ independently represent a $C_1$-$C_6$ alkyl group,
A, A', A'', A''' and A'''' independently represent a linear or branched $C_1$-$C_{20}$ divalent alkylene group,
$R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (S-III), $$(A'''')\text{-}Si(R_6'')_{d''}(OR_5'')_{c''} \quad \text{(S-III)},$$

c, stands for an integer from 1 to 3,
d stands for the integer 3-c,
c' stands for an integer from 1 to 3,
d' stands for the integer 3-c',
c'' stands for an integer from 1 to 3,
d'' stands for the integer 3-c'',
e stands for 0 or 1,
f stands for 0 or 1,
g stands for 0 or 1,
h stands for 0 or 1,
with the proviso that at least one of the radicals from e, f, g and h is different from 0,
and/or $$R_9Si(OR_{10})_k(R_{11})_m \quad \text{(S-IV)},$$

where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k.

9. The method for dyeing keratinous material according to claim 7, wherein the agent (a) comprises at least two structurally different organic $C_1$-$C_6$ alkoxysilanes.

10. A multi-component packaging unit (kit-of-parts) for dyeing keratinous material, comprising separately prepared:
  a first container comprising an agent (a'), wherein the agent (a') comprises:
    (a1) at least one or more $C_1$-$C_6$ organic alkoxysilanes in an amount of from about 50 to about 65 weight percent, based on a total weight of the agent (a'),
  a second container comprising an agent (a''), wherein the agent (a'') comprises:
    (a2) a pigment suspension according to claim 1, and
  a third container comprising an agent (b''), said agent comprising (b''):
    (b1) a sealing reagent.

11. A multi-component packaging unit (kit-of-parts) for dyeing keratinous material, comprising separately prepared:
  a first container comprising an agent (a), wherein the agent (a) comprises:
    (a1) at least one or more $C_1$-$C_6$ organic alkoxysilanes in an amount of from about 50 to about 65 weight percent, based on a total weight of the agent (a),
  a second container comprising an agent (b'), wherein the agent (b') comprises:
    (b1) a sealing reagent, and
  a third container comprising an agent (b''), the agent (b'') comprising:
    (b2) a pigment suspension according claim 1.

* * * * *